United States Patent [19]
Bellini

[11] Patent Number: 4,776,558
[45] Date of Patent: Oct. 11, 1988

[54] FLOW REGULATOR DEVICE FOR PIPES MADE OF ELASTICALLY DEFORMABLE MATERIAL

[75] Inventor: Gianni Bellini, Medolla, Italy

[73] Assignee: Guparo S.r.l., Mirandola, Italy

[21] Appl. No.: 73,313

[22] Filed: Jul. 13, 1987

Related U.S. Application Data

[63] Continuation of Ser. No. 835,383, Mar. 3, 1986, abandoned.

[30] Foreign Application Priority Data

Mar. 4, 1986 [IT] Italy .............................. 28922/85[U]

[51] Int. Cl.⁴ ................................................ F16K 7/06
[52] U.S. Cl. ............................................ 251/9; 251/4
[58] Field of Search .................................. 251/4, 7–10, 251/9

[56] References Cited

U.S. PATENT DOCUMENTS

| | | |
|---|---|---|
| 636,971 | 11/1899 | Forcier ...................................... 251/8 |
| 860,344 | 7/1907 | Towne ..................................... 251/10 |
| 2,366,424 | 1/1945 | Perry ........................................ 251/8 |
| 2,387,660 | 10/1945 | Hall et al. ............................... 251/9 |
| 2,908,476 | 10/1959 | Hidding . |
| 2,931,387 | 4/1960 | Fleming ................................... 251/9 |
| 3,042,067 | 7/1962 | Hidding . |
| 3,477,686 | 11/1969 | Engelsher et al. . |
| 3,544,060 | 12/1970 | Stoltz et al. ............................. 251/9 |
| 3,584,830 | 6/1971 | Koehn ..................................... 251/10 |
| 4,061,142 | 12/1977 | Tuttle ...................................... 251/9 |
| 4,078,583 | 3/1978 | Ragbovachari et al. ........... 251/9 X |
| 4,091,815 | 5/1978 | Larsen .................................... 251/10 |
| 4,241,538 | 12/1980 | Lahr ........................................ 251/9 |
| 4,328,946 | 5/1982 | Morin . |
| 4,410,164 | 10/1983 | Kamen . |
| 4,429,852 | 2/1984 | Tersteegen et al. . |
| 4,467,997 | 8/1984 | Ziaylek, Jr. ........................... 251/10 |

FOREIGN PATENT DOCUMENTS

| | | |
|---|---|---|
| 24378 | 4/1977 | Australia . |
| 1410342 | 7/1964 | France . |
| 1249996 | 8/1964 | France . |
| 1444799 | 5/1965 | France . |
| 853757 | 5/1980 | France . |
| 1097778 | 12/1984 | Fed. Rep. of Germany . |
| 1477944 | 4/1945 | United Kingdom . |
| 1242222 | 7/1945 | United Kingdom . |
| 1381801 | 1/1960 | United Kingdom . |
| 1232587 | 5/1964 | United Kingdom . |
| 1537647 | 10/1971 | United Kingdom . |
| 1240440 | 4/1977 | United Kingdom . |
| 2006927 | 6/1978 | United Kingdom . |

Primary Examiner—A. Michael Chambers
Assistant Examiner—John C. Fox
Attorney, Agent, or Firm—Mary R. Jankousky; Paul C. Flattery; Kay H. Pierce

[57] ABSTRACT

The flow regulator device comprises an internally threaded plug, a punch, a blade and a body. The body has a substantially parallelepipedal form defining a "C"-like cross section and a tower portion terminating in an externally threaded cylindrical tract, adapted for threadedly engaging the plug. The punch protrudes from the plug and is adapted for acting on the blade. The blade projects internally from the body and is adapted for exerting force on a pipe wherein the flow rate is to be controlled.

16 Claims, 1 Drawing Sheet

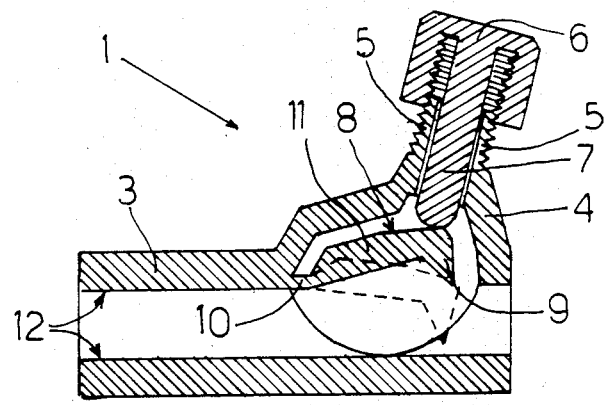
Fig. 1
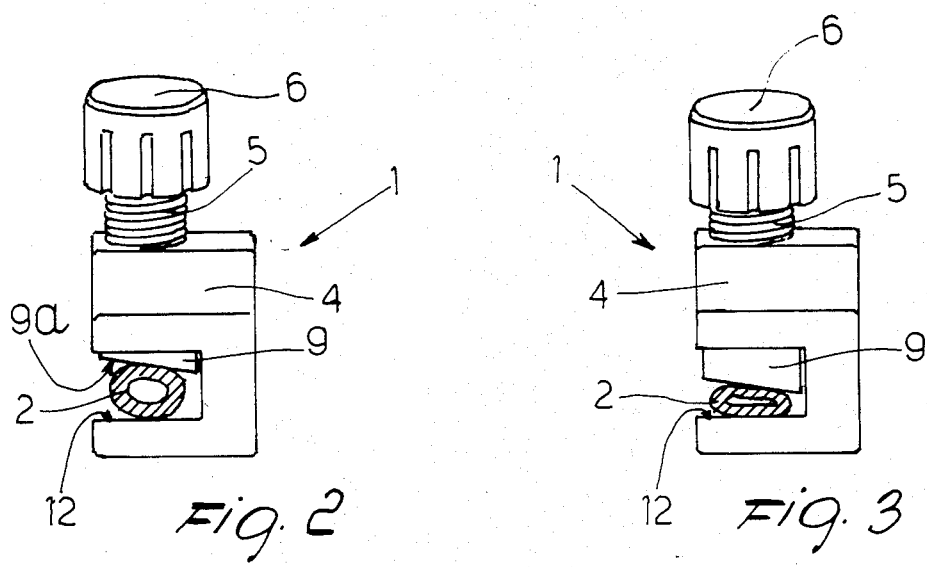
Fig. 2  Fig. 3
Fig. 4  Fig. 5

FLOW REGULATOR DEVICE FOR PIPES MADE OF ELASTICALLY DEFORMABLE MATERIAL

This is a continuation of Ser. No. 835,383, filed Mar. 3, 1986, now abandoned.

BACKGROUND OF THE INVENTION

The present invention relates to a flow regulator device for pipes made of elastically deformable material.

As is known, in many cases it becomes necessary, when working with pipelines or pipes of various types, in particular those made of elastically deformable material, to arrange therein devices which permit regulation of the flow of liquid being delivered according to contingent requirements in its use.

Particularly in the field of medicine, extensive use is made of pipes of generally small and medium diameter which are manufactured of aseptic and elastically deformable material, and carry medicaments or other fluids from containers to patients; and it is in this particular field that the necessity is most felt, to provide flow regulators which are precise in operation, which are of simple construction and of notably low cost.

SUMMARY OF THE INVENTION

Accordingly, an aim of the present invention is to provide a flow regulator device for pipes made of elastically deformable material which in operation permits precise regulation of the flow of fluid passing through the pipe and hence the administered dosage.

Within the above aim, it is an object of the invention to provide a flow regulator device for pipes made of elastically deformable material which is of simple construction and of notably low cost.

This aim and this and other objects which will become apparent hereinafter are achieved by a flow regulator device for pipes made of elastically deformable material which is characterized in that it comprises a threaded plug, a punch, a blade and a body, said body having a substantially parallelepipiedal form defining a "C"-like cross section and having, at an extremity thereof a tower portin terminating in a threaded cylindrical tract, adapted for threadedly engaging said threaded plug, said punch protruding from said plug and being adapted for extending towards the centre of said body and acting on said blade, said blade internally projecting from said body and being adapted for exerting a transverse force on a pipe wherein the flow rate is to be controlled.

BRIEF DESCRIPTION OF THE DRAWINGS

Further features and advantages will be apparent from the following detailed description of a preferred embodiment of the flow regulator device for pipes made of elastically deformable material according to the invention, and the accompanying illustrative non-limitative drawings wherein:

FIG. 1 is a longitudinal sectional view of the flow regulator device according to the invention, as taken on a vertical mid-plane thereof; and FIGS. 2 to 5 each respresent a perspective front view of the flow regulator device according to the invention as applied to an elastically deformable pipe, showing various degrees of intervention thereon.

DESCRIPTION OF THE PREFERRED EMBODIMENTS

With reference to the above cited drawing figures, generally illustrated by the reference numeral 1 is a flow regulator device for pipes 2 made of elastically deformable material which comprises a body 3 of substantially parallelepipedal form defining a "C"-like cross section, having at an extremity thereof a tower-like member or tower portion 4 which terminates in a cylindrical tract 5, threaded externally and projecting outwardly, for thread engagement relationship with a punch or plug 6, which is counter-threaded at an interior portion thereof and is provided centrally with a punch 7, having a rounded extremity adapted to engage, in abutment engagement, with an upper face 8 of a blade or guillotine 9, located below the plug 6 and being expediently formed integrally with, and protruding from an internal wall of said body 3.

Advantageously, the front 9a of the blade 9 is slightly inclined and adapted to exert a transverse force or pressure on the pipe 2, to squeeze or compress the same.

The blade 9 also has a first narrowed flexible attachment portion 10, elastically attached to the body 3, followed by an enlarged portion or pad 11 which extends to the front 9a of said blade 9.

The particular "C"-like cross sectional configuration of the body of the device according to the invention, gives rise to the definition of a seat 12, open at one side, such that a tract of pipe 2, wherein it is desired to control the delivery flow rate, may be inserted into said seat 12.

The operation of the flow regulator device will be appreciated from the preceding description. When the plug 6 is fully unscrewed, one may apply the device 1 to a pipe 2 by introducing a tract or portion of the pipe 2 into the seat 12.

One then acts on the cited plug 6, screwing the same onto the cylindrical threaded tract 5 of the tower portion 4, thus causing the threads formed on the interior of the plug 6 to engage the threads of said threaded tract, to cause a downward movement of the punch 7, resultantly causing the latter to exert a pressure force on the upper face 8 of the blade 9, which is in turn permitted to be pushed downwards at its front edge 9a by virtue of its attachment at the narrowed portion 10 to the body 3.

Such movement causes the front 9a of the blade 9 to squeeze the pipe 2 and, being slightly inclined, the squeezing action exerted by the blade 9 on the tube 2 is differentiated in that such squeezing action is more accentuated at one part of the section of the pipe 2, than at the part thereof which is diametrically opposite.

This permits one to obtain even minute flow rates and hence dosages without causing damage to the body of the pipe, which can, if required, be also totally occluded.

Some of the many various possible degrees of intervention of the blade 9 on the pipe 2 are shown in FIGS. 2,3,4, and 5.

It should be noted that the device according to the invention avails itself of particular economical characteristics, owing to the fact that it may be obtained by hot stamping just two components.

It has been found in practice that the invention fully achieves its aim and object.

The invention as disclosed herein is susceptible to numerous modifications and adaptations, all falling within the purview of the inventive concept.

Furthermore, all of the details may be substituted by technically equivalent elements.

In practice, any materials, dimensions and contingent shapes may be used according to contingent requirements, without departing from the scope of protection of the following claims

I claim:

1. A flow regulator device for pipes which is characterized in that it comprises a threaded plug, a punch, and a body, said body made of elastically deformable material substantially defining a "C"-like cross section and having a tower portion terminating in a threaded cylindrical tract, adapted for threadedly engaging said threaded plug, said body having a blade integrally formed in said body within said "C"-like cross section, said punch protruding from said plug and being adapted for extending towards the center of said body and acting on said blade, said blade having a slightly inclined front edge ending in a pointed tip, said front edge exerting a transverse force on a pipe wherein the flow rate is to be controlled.

2. A flow regulator device according to claim 1, characterized in that said plug has a rounded extremity adapted for abutment engagement with the upper face of said blade.

3. A flow regulator device according to claim 1, characterized in that said blade comprises a narrowed portion for flexibly attaching said blade to said body at an interior portion thereof and an enlarged portion extending between said narrowed portion and said front edge.

4. A flow regulator device for pipes which is characterized in that it comprises a threaded plug, a punch, and a body, said body made of elastically deformable material substantially defining a "C"-like cross section and having a tower portion terminating in a threaded cylindrical tract, adapted for threadedly engaging said threaded plug, said body having a blade integrally formed in said body within said "C"-like cross section, said blade comprising a narrowed portion and an enlarged portion, said narrowed portion flexibly attaching said blade to said body at an interior portion thereof, said punch protruding from said plug and being adapted for extending towards the center of said body and acting on said blade, said blade having a slightly inclined front edge with a pointed tip, said front edge exerting a transverse force on a pipe wherein the flow rate is to be controlled.

5. A flow regulator device for elastically deformable pipes, said flow regulator device moving between an open position and a closed position, said flow regulator comprising:
   a body formed of a single component, said body including:
   a lower wall;
   a side wall;
   a top wall with a cutaway portion, said lower wall, side wall, and top wall forming a seat for the pipe;
   a tower portion positioned over the cutaway portion of said top wall, said tower portion terminating in a threaded cylindrical tract, aid tower portion having a hole extending therethrough;
   a blade positioned within said tower portion, said blade being connected to said top wall by a narrowed flexible attachment portion, said blade extending approximately coextensive with said top wall, said blade allowing free placement of the pipe in the seat in the flow regulator open position, said blade including a downwardly inclined front edge having a pointed tip; and
   a plug with threads mating with the threads of said tower portion, said plug having a punch that extends through said tower portion hole, upon the roation of said plug in a given direction said punch contacts said blade to force the pointed tip into contact with the pipe and the flow regulator device towards the closed position.

6. A flow regulator device as claimed in the claim 5 wherein said blade has an upper face with a cammed surface, whereupon the rotation of said plug in a given direction said punch contacts said blade upper face.

7. A flow regulator device as claimed in claim 5 whereupon in the flow regulator device closed position, said blade exerts unequal squeezing action on that side of the pipe adjacent said side wall and on that side of the pipe farthest from said side wall.

8. A flow regulator device as claimed in claim 5 wherein no portion of said blade extends outside the cutaway portion of said top wall.

9. A flow regulator device as claimed in claim 5 wherein no substantial portion of said blade is positioned below said top wall in said flow regulator device open position.

10. A flow regulator device as claimed in claim 8 wherein no substantial portion of said blade is positioned below said top wall in said flow regulator device open position.

11. A flow regulator device for elastically deformable pipes, said flow regulator device moving between an open position and a closed position, said flow regulator comprising:
   a body including:
   a lower portion;
   a top portion with a tower portion, said lower portion and said top portion forming a seat for the pipe, said tower portion terminating in a threaded tract, said tower portion having a hole extending therethrough;
   a blade positioned between said lower portion and said top portion, said blade being connected to said top portion by a flexible attachment portion, said blade allowing placement of the pipe in the seat in the flow regulator open position, said blade including a downwardly inclined front edge having a pointed tip; and
   a plug having threads mating with the threads of said tower portion, said plug having a punch that extends through said tower portion hole, whereupon the rotation of said plug in a given direction said punch contacts said blade to force the pointed tip into contact with the pipe and the flow regulator device towards the closed position.

12. A flow regulator device as claimed in the claim 11 wherein said blade has an upper face with a cammed surface, whereupon the rotation of said plug in a given direction said punch contacts said blade upper face.

13. A flow regulator device as claimed in claim 11 whereupon in the flow regulator device closed position, said blade exerts unequal squeezing action across the width of the pipe.

14. A flow regulator device as claimed in claim 11 wherein substantially no portion of said blade extends outside the area between the top portion and the lower portion.

15. A flow regulator device as claimed in claim 11 wherein the pointed tip of said blade front edge is not horizontal.

16. A flow regulator device as claimed in claim 11 wherein said blade is substantially parallel with said top portion in the flow regulator open position.

* * * * *